(12) United States Patent
Onobori

(10) Patent No.: US 12,376,739 B2
(45) Date of Patent: Aug. 5, 2025

(54) ENDOSCOPIC ILLUMINATION SYSTEM FOR FLUORESCENT AGENT

(71) Applicant: HOYA CORPORATION, Tokyo (JP)

(72) Inventor: Kunihiko Onobori, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 477 days.

(21) Appl. No.: 18/013,140

(22) PCT Filed: Jun. 24, 2021

(86) PCT No.: PCT/IB2021/055595
§ 371 (c)(1),
(2) Date: Dec. 27, 2022

(87) PCT Pub. No.: WO2022/003506
PCT Pub. Date: Jan. 6, 2022

(65) Prior Publication Data
US 2023/0240521 A1    Aug. 3, 2023

(30) Foreign Application Priority Data
Jul. 3, 2020   (DE) .................. 10 2020 117 579.5

(51) Int. Cl.
A61B 1/07    (2006.01)
A61B 1/05    (2006.01)
A61B 1/06    (2006.01)

(52) U.S. Cl.
CPC .............. A61B 1/07 (2013.01); A61B 1/05 (2013.01); A61B 1/06 (2013.01); A61B 1/0638 (2013.01); A61B 1/0646 (2013.01)

(58) Field of Classification Search
None
See application file for complete search history.

(56) References Cited

U.S. PATENT DOCUMENTS 11,559,194 B2    1/2023   Onobori
2006/0058584 A1  3/2006   Hirata
(Continued)

FOREIGN PATENT DOCUMENTS

EP   2433556 A1      3/2012
JP   5977913 B1      7/2016
JP   2019-072328 A   5/2019
(Continued)

OTHER PUBLICATIONS

Kobayashi, H. et al., "Near-Infrared Photoimmunotherapy of Cancer", Accounts of Chemical Research, vol. 52, Jul. 23, 2019, pp. 2332-2339.
(Continued)

Primary Examiner — John P Leubecker
(74) Attorney, Agent, or Firm — GREENBLUM & BERNSTEIN, P.L.C.

(57) ABSTRACT

An illumination apparatus for outputting an output light includes a first light source configured to emit first light with a first peak wavelength in a first range of 660 nm to 699 nm and a second light source configured to emit second light with a second peak wavelength in a second range of 689 nm to 705 nm. The second peak wavelength is larger than the first peak wavelength by at least 5 nm and the second light source is configured to be switched on and off independently from the first light source. The apparatus is configured to output the first light as the output light if the second light source is switched off and to output the first light and the second light as the output light if the second light source is switched on.

13 Claims, 8 Drawing Sheets

(56) References Cited

U.S. PATENT DOCUMENTS

| | | |
|---|---|---|
| 2008/0089089 A1 | 4/2008 | Hama et al. |
| 2012/0200687 A1 | 8/2012 | Kikuchi |
| 2013/0002167 A1 | 1/2013 | Van De Ven |
| 2014/0240468 A1* | 8/2014 | Feke ............... H04N 7/18 348/47 |
| 2017/0032521 A1* | 2/2017 | Kubo ............... A61B 1/00009 |
| 2019/0071506 A1 | 3/2019 | Barth et al. |
| 2019/0388702 A1* | 12/2019 | Watanabe ........ A61K 49/0036 |
| 2021/0059532 A1* | 3/2021 | Tsumatori ........... A61B 5/0084 |
| 2021/0106211 A1 | 4/2021 | Onobori |
| 2021/0267439 A1 | 9/2021 | Onobori et al. |
| 2022/0096862 A1* | 3/2022 | Yoshino ............ A61N 5/062 |
| 2022/0225862 A1 | 7/2022 | Onobori |
| 2022/0288411 A1* | 9/2022 | Tsumatori ........... A61N 5/062 |
| 2023/0008437 A1* | 1/2023 | Sawada ............ A61B 5/0071 |
| 2023/0014312 A1* | 1/2023 | Suehara ........... A61N 5/0603 |
| 2023/0082243 A1 | 3/2023 | Onobori |

FOREIGN PATENT DOCUMENTS

| | | |
|---|---|---|
| WO | 2019/244977 A1 | 12/2019 |
| WO | WO 2020/054634 A1 | 3/2020 |

OTHER PUBLICATIONS

U.S. Appl. No. 18/013,153 to Kunihiko Onobori et al., filed Dec. 27, 2022.

U.S. Appl. No. 18/023,052 to Wolfgang Mayer et al., filed Feb. 24, 2023.

International Search Report issued in International Patent Application No. PCT/IB2021/055595, dated Oct. 18, 2021.

Notice of Reasons for Refusal issued in Japanese Patent Application No. 2022-579879, dated Jan. 16, 2024, together with an English translation.

Notice of Reasons for Refusal issued in Japanese Patent Application No. 2024-039363, dated Dec. 10, 2024, together with an English translation.

\* cited by examiner

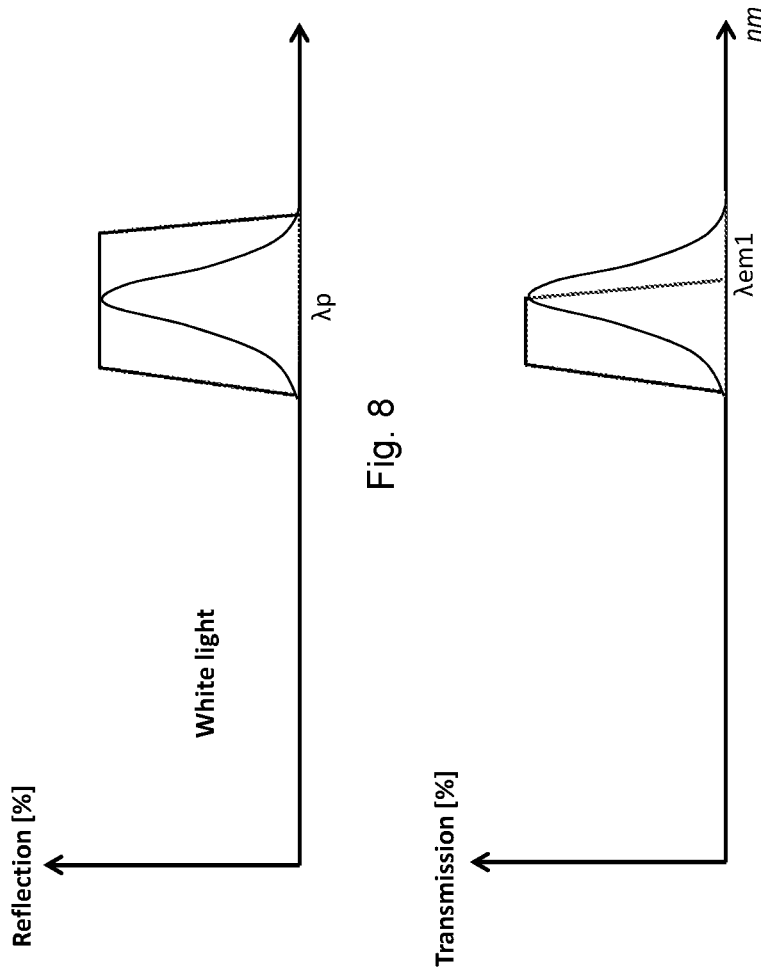
Fig. 8
Fig. 9
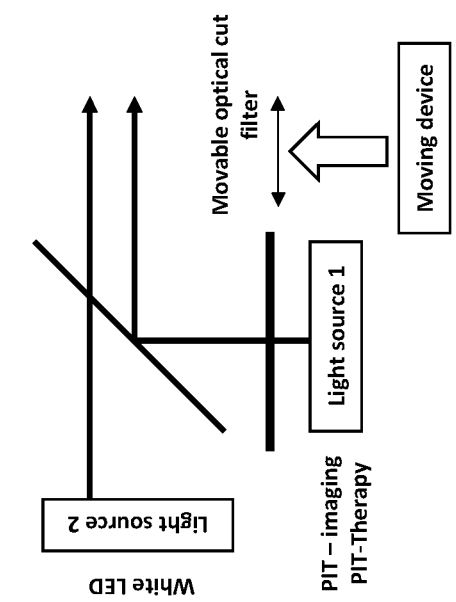
Fig. 7

ENDOSCOPIC ILLUMINATION SYSTEM FOR FLUORESCENT AGENT

NIR-PIT (Near infrared photo immunotherapy) is expected as a new cancer therapy. The drug for NIR-PIT has conjugate structure with IRDye700DX (hereinafter: IR700) as a photo reactor and antibody drug. The main functions of the drug are drug delivery system (DDS) for molecular target therapy, fluorescence imaging with well differentiation against auto fluorescence (510 nm) and therapy (see https://www.ncbi.nlm.nih.gov/pmc/articles/PMC6704485/).

Excitation and emission characteristics of IR700 are shown in FIG. 1. As the graph shows, peak wavelengths of excitation sensitivity (maximum excitation sensitivity at $\lambda_{p,ex}$=689 nm) and of emission of fluorescence light ($\lambda_{p,em}$=699 nm) are very close to each other.

When it is intended to image a scene by fluorescence light from IR700 which is excited by excitation light, the excitation light should have a wavelength close to the emitted fluorescence light. However, such excitation light disturbs the imaging by the fluorescence light. A separation of these two lights such that the imaging system gets enough fluorescence signal without a lot of excitation light is difficult.

On the other hand, for therapeutic usage, a high specific energy accumulation such as 50 J/cm$^2$ at the peak excitation wavelength of IR700 (689 nm) and a few nm around the peak excitation wavelength is required. Otherwise, it may take a long time to make therapeutic reaction.

The requirements for imaging and for therapeutic usage are in conflict with each other if imaging and therapy are to be performed by a single endoscope.

CIE 1931 links between distributions of wavelengths in the electromagnetic visible spectrum and physiologically perceived colors in human color vision. FIG. 2 shows a gamut according to CIE1931 (x-y-plane, taken from people.cs.clemson.edu). The area in the middle (without color notations) denotes whitish light. The numbers at the border of the gamut indicate the wavelength (in nm) of the respective spectral clean light. White light has the coordinates x=⅓; y=⅓; and z=⅓.

SUMMARY OF THE INVENTION

It is an object of the present invention to improve the prior art.

The present invention provides an improved illumination system allowing both imaging based on fluorescence from IR700 and therapeutic usage of IR700, e.g. for cancer therapy.

It is provided an illumination apparatus for outputting an output light, comprising a first light source configured to emit first light with a first peak wavelength in a first range of 660 nm to 699 nm; a second light source configured to emit second light with a second peak wavelength in a second range of 689 nm to 705 nm; wherein the second peak wavelength is larger than the first peak wavelength by at least 5 nm; the second light source is configured to be switched on and off independently from the first light source; the apparatus is configured to output the first light as the output light if the second light source is switched off and to output the first light and the second light as the output light is the second light source is switched on.

BRIEF DESCRIPTION OF THE DRAWINGS

Further details, features, objects, and advantages are apparent from the following detailed description of the preferred embodiments of the present invention which is to be taken in conjunction with the appended drawings, wherein:

FIG. 7 shows an illumination apparatus according to an embodiment of the invention;

FIG. 8 shows the reflectivity of the dichroic interface (dichroic mirror) used in the illumination apparatus of FIG. 7;

FIG. 9 shows the transmission through the optical cut filter included in the illumination apparatus of FIG. 7;

DETAILED DESCRIPTION OF CERTAIN EMBODIMENTS

Figure 1:
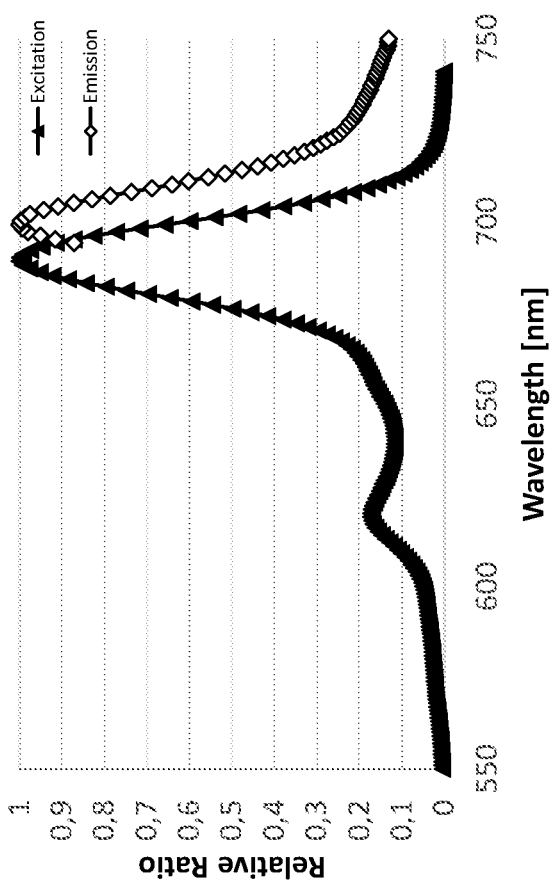
FIG. 1 shows excitation spectrum and emission spectrum of IR700.
Figure 2:
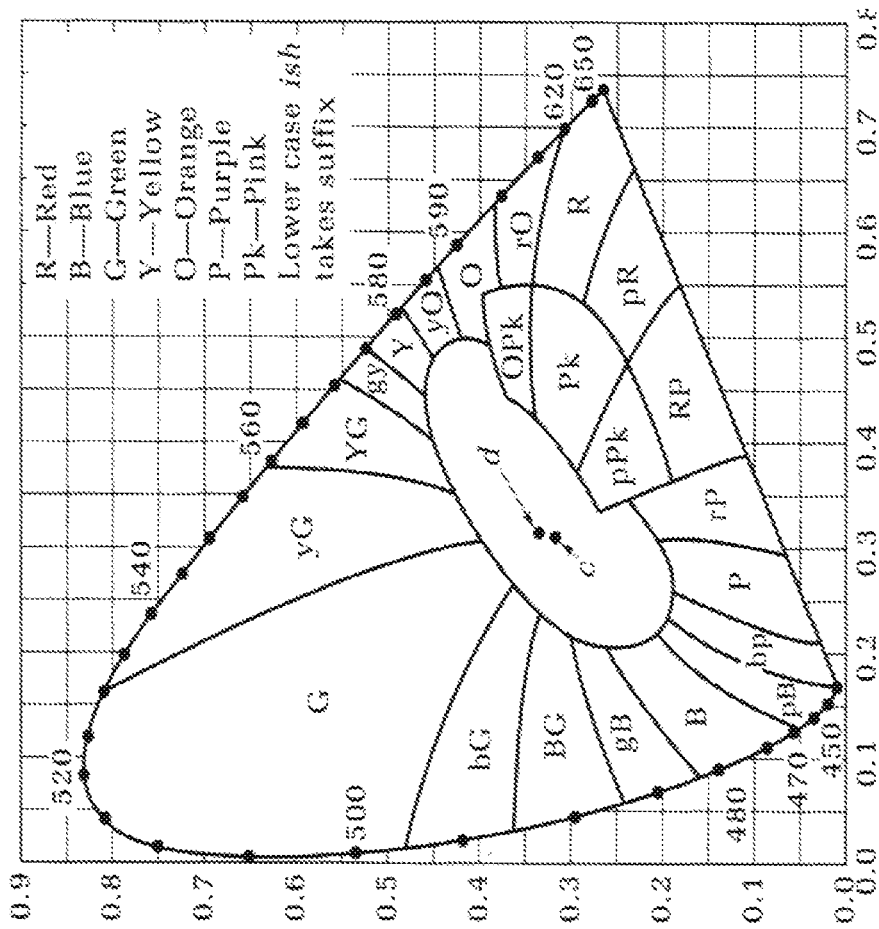
FIG. 2 shows a gamut according to CIE 1931.

Herein below, certain embodiments of the present invention are described in detail with reference to the accompanying drawings, wherein the features of the embodiments can be freely combined with each other unless otherwise described. However, it is to be expressly understood that the description of certain embodiments is given by way of example only, and that it is by no way intended to be understood as limiting the invention to the disclosed details.

First Embodiment

According to a first embodiment, the illumination apparatus has at least two light sources:

Light source 1 has a peak wavelength 660 nm≤λp1<699 nm. It may be used for both fluorescent imaging and therapeutic usage. The peak wavelength is shorter than the emission peak wavelength from IR700 (699 nm) and shorter than the peak wavelength of "Light source 2".

Light source 2 has a peak wavelength 689 nm≤λp2<705 nm. It is typically used for therapeutic usage only. The peak wavelength of the light source 2 is larger than that of the light source 1. For example, it may be larger by at least 5 nm, preferably by at least 10 nm, and more preferably by at least 15 nm.

For fluorescent imaging of a scene, only light source 1 is typically used. Thus, the light at wavelengths of 700 nm and larger wavelengths coming from the scene mainly results from fluorescence by IR700.

In therapeutic usage, both "Light source 1" & "Light source 2" are typically turned on to boost therapeutic reaction of PIT. Thus, the procedure time is reduced compared to illumination with one of the light sources only to reduce the burden for patients and medical professionals.

The light sources 1 and 2 typically may be laser diodes or LEDs. Examples of light source 1 are laser diode L690-66-60 (from USHIO OPTO SEMICONDUCTORS, INC); and MRL-III-690 (see http://www.cnilaser.com/red_laser690.htm).

An example of light source 2 is laser diode MLL-FN-698 (see http://www.cnilaser.com/Red-Laser-698 nm.htm).

In addition, the apparatus may comprise a light source 3 for another imaging mode, such as white light imaging. For white light imaging, the third light source 3 emits light such that the light is closer to the white point (x=y=z=⅓) of CIE 1931 than the light from the first light source. The term "closer to the white point" means a shorter Euclidian distance in the x-y-plane of the gamut of CIE1931 from the white point x=y=⅓ (the z-direction is ignored). The Euclidian distance of an illumination light with coordinates $x_i$, $y_i$ in the x-y-plane from the white point is $(x_i-⅓)^2+(y_i-⅓)^2$.

White light imaging is just one example of another imaging mode. If appropriate, instead of (or in addition to) white light imaging, imaging with colored light or with UV light or with (far) infrared light (in general: spectrum imaging) may be performed.

The lights from the two or three light sources are combined by a combiner. For two light sources, a dichroic mirror may be used. For three light sources, two dichroic mirrors may be used. The two dichroic mirrors may be functionally combined in a crosscube comprising two dichroic interfaces.

Figure 3:
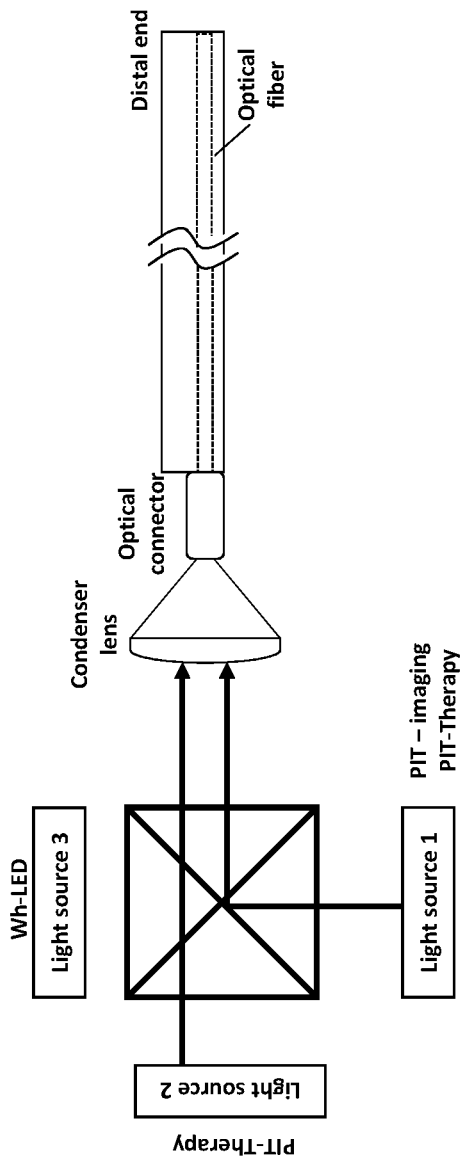
FIG. 3 shows an illumination apparatus according to an embodiment of the invention.
Figure 4:
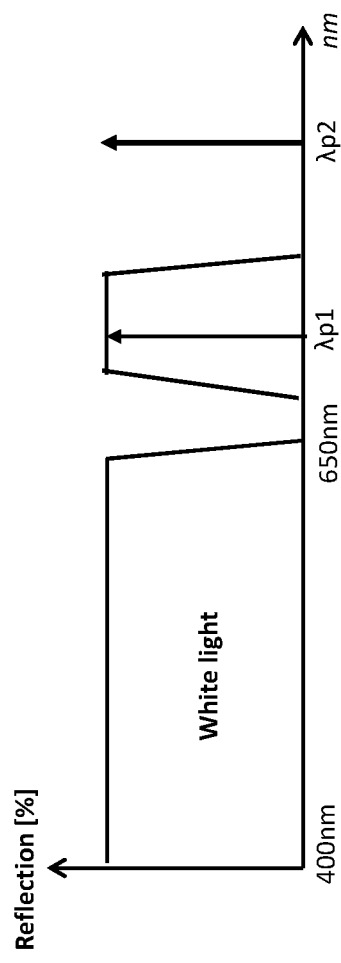
FIG. 4 shows the reflectivity of the dichroic interfaces of the crosscube used in the illumination apparatus of FIG. 3.

FIG. 3 shows an embodiment of such an illumination apparatus. FIG. 4 shows the reflectivity of the dichroic interfaces of the crosscube used in the illumination apparatus of FIG. 3. As can be seen from FIG. 3, the light from the light source 1 and the light from the light source 3 are reflected at respective dichroic interfaces of the crosscube. The light from light source 2 passes through both dichroic interfaces. Accordingly, in this example, one of the dichroic interfaces reflects light around the peak wavelength λp1 of the first light source, and the other of the dichroic interfaces reflects white light, e.g. in a range of 400 nm to 650 nm, as shown in FIG. 4. The reflection bands are typically separated from each other. The dichroic interfaces pass light of other wavelengths such as of the peak wavelength λp2 of the second light source and of wavelengths around λp2.

The combined light may be condensed by a condenser (such as a convex lens) on an optical connector which inputs the light into an optical fiber to illuminate a scene. For example, the emission end of the optical fiber may be arranged in a distal rigid tip portion of an endoscope to illuminate a scene which is imaged by an imaging device (objective lens) arranged in the rigid tip portion of the endoscope.

Figure 13:
FIG. 13 shows an illumination apparatus according to an embodiment of the invention.
Figure 14:
FIG. 14 shows an illumination apparatus according to an embodiment of the invention.
Figure 12:
FIG. 12 shows an illumination apparatus according to an embodiment of the invention

If the illumination apparatus is arranged close to the scene to be illuminated, e.g. if the illumination apparatus is arranged in the rigid tip portion of an endoscope, the condenser, optical connector, and optical fiber may be omitted. FIGS. 12 to 14 provide respective examples. In this case, light source 1 and light source 2 are typically LEDs, e.g. based on AlGaInP material. Some embodiments comprise two different types of LEDs. In some embodiments, LED1 may be of the same type as LED2, but covered with a filter correspondingly to the filter described further below with respect to FIG. 7.

As shown in FIG. 12, the illumination apparatus provided in the rigid tip portion at the distal end of an endoscope comprises only LED1 and LED2 arranged on one or two circuit boards. In addition, the illumination apparatus may comprise further LEDs such as a blue LED and a violet LED, as shown in FIG. 13. Still furthermore, the LEDs may be covered by a phosphor layer and/or a transparent cap, as shown in FIG. 14. Preferably, the phosphor layer has an excitation spectrum such that fluorescence or luminescence is not excited by the light from LED1 or LED2. I.e., for the light from LED1 and LED2, the phosphor layer is substantially transparent.

In some embodiments, the lights of even more light sources with different peak wavelengths may be combined through an appropriate number of dichroic reflective interfaces (n light sources→n−1 dichroic reflective interfaces). Up to four dichroic interfaces may be arranged jointly in a respective crosscube (two dichroic interfaces to reflect lights from first and second light sources arranged in a first plane comprising the propagation direction of the output light, and two dichroic interfaces to reflect lights from third and fourth light sources arranged in a second plane comprising the propagation direction of the output light, wherein the first plane intersects the second plane; typically, the second plane is perpendicular to the first plane).

Figure 6:
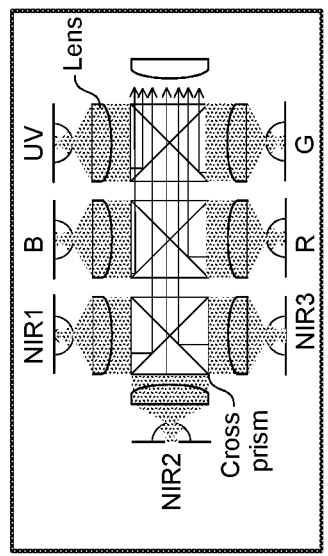
FIG. 6 shows an illumination apparatus according to an embodiment of the invention.

An example of such an illumination apparatus is shown in FIG. 6. In FIG. 6, each of the three crosscubes (in general: crossprisms) has two dichroic interfaces. The lights of three near infrared (NIR) light sources NIR1, NIR2, and NIR3 are combined by the first crosscube, and the second and third crosscubes combine RGB lights (red, green, blue) and UV light (ultraviolet) with the light output by the first crosscube. Through the RGB lights, white light imaging may be achieved. The UV light, potentially together with the green light, may be used for enhanced vascular imaging. In the example of FIG. 6, the lights from the light sources are collimated by respective lenses before they enter the respective crosscube. The arrangement of the light sources may be changed if the dichroic reflective interfaces have appropriate reflection characteristics. For example, some or all of the RGB light sources may exchange their positions with the positions of the NIR light sources.

In general, each of the light sources of the illumination apparatus may be separately controllable. That is, each of them may be switched on and off independently from the other light sources. In addition, in some embodiments, the light intensity or the emitted color of at least one of the light sources may be controlled independently from the other light sources. Some embodiments include a controller to perform the controlling.

For example, if only the first light source is switched on, the illumination apparatus may illuminates a scene to be imaged on an imaging surface. For the imaging, an imaging device may be used. The imaging device typically comprises an objective lens for imaging the scene on the imaging surface. However, the imaging device is not limited to a lens optic but it may comprise e.g. reflective components (catoptric system).

Furthermore, in some embodiments, the imaging device comprises a filter (excitation light cut filter) which may be a band filter. Namely, in the wavelength range between 670 nm and 715 nm, this filter passes fluorescence light from IR700 (i.e. a wavelength band in a range above 699 nm and below 715 nm) and blocks the excitation light in the range below 699 nm. Thus, the excitation light does not disturb (or hardly disturbs) the image of the fluorescence light. In general, the filter may block light below a preset wavelength which is in the range of 690 nm to 700 nm and passes light above the preset wavelength.

Figure 5:
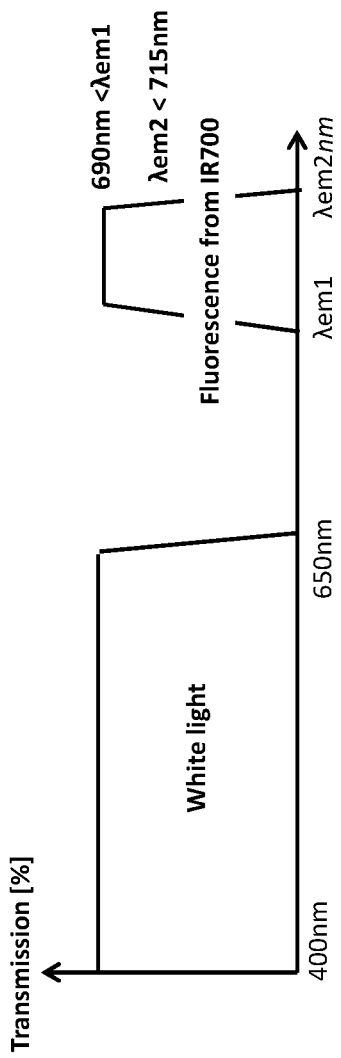
FIG. 5 shows the transmission through a filter included in an imaging system according to some embodiments of the invention.

In addition, as shown in FIG. 5, the filter may pass white light (wavelength below 650 nm) from the third light source such that the same imaging device may be used for fluorescence imaging through illumination by the first light source and white light imaging through illumination by the third light source.

The image on the imaging surface may be captured by an image sensor, such as a CMOS array or a CCD array. In some embodiments, the image on the imaging surface may be observed directly or via a relay optic.

In some embodiments, the beam may be divided by a further dichroic mirror. The further dichroic mirror may reflect the fluorescence light such that the fluorescence image may be observed by a first image sensor while other light is blocked from the first image sensor. The further dichroic mirror may pass other light such as white light (or one of the RGB lights) or UV light from one or more of the other light sources. Thus, the image due to the illumination with the other light may be observed by a second image sensor. The observations may be performed simultaneously on the first and second image sensors. In some embodiments, the further dichroic mirror may pass the fluorescence light and reflect the other light instead of the above described configuration.

Figure 15:
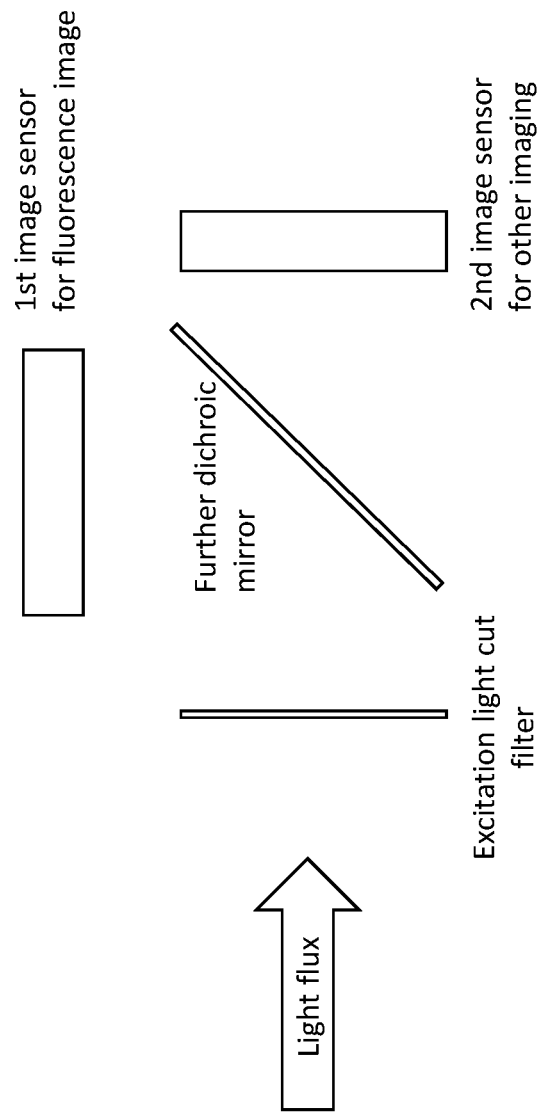
FIG. 15 shows a sensor system which may be used in an imaging system according to some embodiments of the invention.

In addition, the sensor configuration may comprise an excitation light cut filter (such as the one described hereinabove) to filter the excitation light, in particular if the further dichroic mirror does not include a corresponding filter function. Such a sensor configuration is shown in FIG. 15. The objective lens and other optical components are omitted from FIG. 15 for the sake of clarity. In this case, the excitation light cut filter passes light having a wavelength of at least 20 nm below the preset wavelength. Preferably, the difference is even larger (e.g. 40 nm or even 60 nm) such that hardly any excitation light passes the excitation light cut filter, while white light (or any of RGB light) or UV light passes the excitation light cut filter.

Second Embodiment

Hereinafter, differences between the second embodiment and the first embodiment are described. If not otherwise stated or made clear from the context, the description of the first embodiment applies to the second embodiment, too.

In the second embodiment, as shown in FIG. 7, the illumination apparatus comprises only one NIR light source (first light source) having a peak wavelength $\lambda p1$ in the range 660 nm$\leq \lambda p1<$700 nm and an emission spectrum which extends beyond 700 nm with at least 30% of the intensity at the peak wavelength.

In addition, an optical filter (e.g. a bandpass filter) is located on the light path between the light source and the output of the illumination apparatus (e.g. between the light source and the light connector). The bandpass filter is movable such that it may be in the light path or outside the light path. The bandpass filter passes the excitation light and blocks substantially light in the wavelength range of the fluorescence light emitted by IR700. For example, the bandpass filter may pass light of a wavelength less than a predefined wavelength and block light of a wavelength larger than the predefined wavelength, wherein the predefined wavelength is in a range between 689 nm and 700 nm.

In order to be effective as a filter, the light intensity of the first light source at the predefined wavelength is at least 50% of the light intensity at the peak wavelength of the light from the first light source. Preferably, it is at least 65%, or even at least 80%.

The filter may be moved into and out of the light path by a moving device. The moving device may be e.g. a motor. The motor may be controlled by a controller. The moving device may be e.g. a handle or some other mechanism such that the filter may be moved manually. The movement may be e.g. a linear movement or a rotational movement. If the filter is moved out of the light path, the light output from the illumination apparatus comprises the light from the light source without having passed through any filter filtering out more than 30% of the light intensity of any wavelength in the relevant wavelength range between 680 nm and 720 nm.

If the filter is in the light path, the one light source may be used for imaging because the light from the light source corresponding to the fluorescence light is substantially blocked. If the bandpass filter is not in the light path, the light source may be used for therapy with a high radiation power.

As shown in FIG. 7, the illumination apparatus of the second embodiment may additionally (optionally) comprise a second light source (e.g. a white light source). The second light source corresponds to the third light source of the first embodiment and may be used e.g. for white light imaging. The lights from the first light source (having filtered by the movable filter, if it is inserted in the light path) and from the second light source may be combined by a dichroic reflective surface (e.g. dichroic mirror). FIG. 8 shows an example of the reflectivity of the dichroic reflective surface when the light from the first light source around the peak wavelength $\lambda p$ (shown schematically in FIG. 8, too) should be reflected and the white light from the white light source should pass through the reflective dichroic surface. The reflection band in this case comprises also (at least a part of) the spectrum from the first light source which may be cut off by the movable filter.

FIG. 9 shows an example of a transmission spectrum of the movable filter. The filter transmits only light of the lower wavelength range from the first light source. In the example of FIG. 9, it transmits substantially only light below the peak wavelength of the light from the first light source. However, this is not mandatory. The transmission band may be set such that sufficient light for exciting the fluorescence of IR700 passes and a sufficiently large portion of light of larger wavelength (corresponding to the fluorescence light) is blocked.

Figure 10:
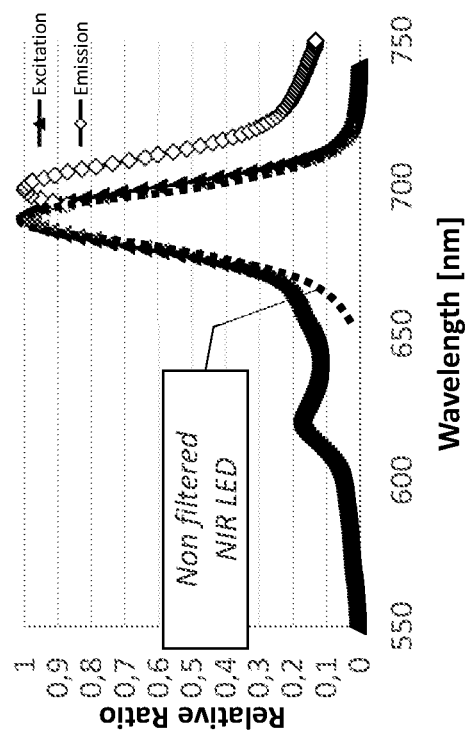
FIG. 10 shows an example spectrum of output light from the illumination apparatus of FIG. 7 if the optical cut filter is removed from the light path over the excitation spectrum and emission spectrum of IR700.

FIG. 10 shows an example of the light emitted by the first light source of the second embodiment (black squares) over the excitation spectrum and emission spectrum of IR700 shown in FIG. 1. In this case, the spectrum of the light from the first light source corresponds substantially to the peak of the excitation spectrum of IR700. Thus, the light from the first light source efficiently excites fluorescence of IR700. A large energy dose may be deposited in the tissue.

Figure 11:
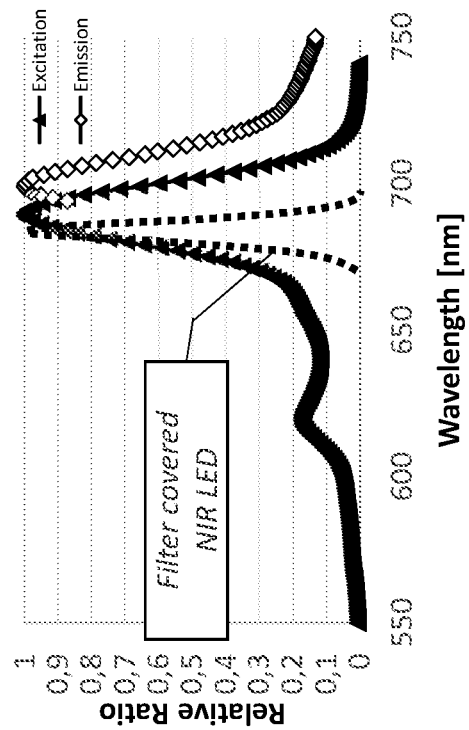
FIG. 11 shows an example spectrum of output light from the illumination apparatus of FIG. 7 if the optical cut filter is in the light path over the excitation spectrum and emission spectrum of IR700.

In contrast, FIG. 11 shows the spectrum of the light from the first light source filtered by the movable filter (black squares) over the excitation spectrum and emission spectrum of IR700 shown in FIG. 1. In this example, the part of the emitted light at larger wavelengths (above about 695 nm) is cut off. Thus, this light still excites fluorescence of IR700 but hardly interferes with the fluorescence light generated by IR700.

The imaging device of the second embodiment may be the same as that of the first embodiment. Also, the illumination apparatus of the second embodiment may comprise further light sources emitting different wavelengths than the first light source, such as one or more RGB light sources, a UV light source, or a (far) IR light source, similar to the illumination apparatus shown in FIG. 6.

The illumination apparatus according to some embodiments of the invention may be arranged in an external box (light source box or processor system). The light from the external box may be guided from the proximal end of the endoscope to the distal tip of the endoscope through one or more optical fibers in order to illuminate an object space of an imaging device (e.g. objective lens) arranged at the distal tip of the endoscope. However, the illumination system may be arranged in a control body, an endoscope connector, or even in the distal tip of an endoscope instead.

In some embodiments, the optical fiber and optics (e.g. optical connector) to direct the light from the illumination apparatus into the optical fiber may be considered as belonging to the output portion of the illumination apparatus. In these embodiments, their influence on the light output from the crosscube may be taken into account when designing the light sources and the combiner(s) such as the dichroic reflective interface(s).

Some embodiments of the invention comprise a combination of a mother scope and a baby scope. Such a combination may be used to approach thin and peripheral area or organ like bronchus. In this case, mother scope behaves as a conventional endoscope. Baby scope is guided by mother scope through the working channel of the mother scope. I.e., the baby scope is much thinner than the mother scope.

The light output from the external box (light source box) may be divided in appropriate proportions to mother scope and baby scope by a beam splitter such that both mother scope and baby scope illuminate the respective scene by a same light. The beam splitter may be a part of the optical connector from the light source box.

The endoscope comprising the illumination apparatus may be a capsule endoscope without a shaft (e.g. rigid or flexible tube) or an endoscope comprising a rigid tip portion at the distal end and a shaft (e.g. rigid or flexible tube). The rigid tip portion may be connected to the shaft directly or indirectly via an angulation segment. The endoscope may be suitable for being inserted into a lumen of a human body.

In some embodiments, the illumination apparatus and potentially also the imaging device may be used ex vivo such that it is not arranged in an endoscope.

The invention claimed is:

1. An illumination apparatus for outputting an output light, comprising
    a first light source configured to emit first light with a first peak wavelength in a first range of 660 nm to 699 nm;
    a second light source configured to emit second light with a second peak wavelength in a second range of 689 nm to 705 nm; wherein
    the second peak wavelength is larger than the first peak wavelength by at least 5 nm;
    the second light source is configured to be switched on and off independently from the first light source;
    the apparatus is configured to output the first light as the output light if the second light source is switched off and to output the first light and the second light as the output light if the second light source is switched on.

2. The illumination apparatus according to claim 1, further comprising
    a first combiner configured to combine the first light from the first light source and the second light from the second light source to output the output light.

3. The illumination apparatus according to claim 2, further comprising
    a white light source configured to emit white light; and
    a white light combiner configured to combine the white light from the white light source such that the output light comprises the white light,
    wherein the white light source is configured to be switched on and off independently from the first light source and, if available, from the second light source, and
    wherein the white light combiner is integral with the first combiner.

4. The illumination apparatus according to claim 2, wherein
    the first light combiner comprises at least one dichroic reflective interface.

5. The illumination apparatus according to claim 1, further comprising
    a white light source configured to emit white light;
    a white light combiner configured to combine the white light from the white light source such that the output light comprises the white light; wherein
    the white light source is configured to be switched on and off independently from the first light source and, if available, from the second light source.

6. An illumination apparatus for outputting an output light, comprising
    a first light source configured to emit first light with a first peak wavelength in a first range of 660 nm to 700 nm;
    a first filter configured to pass light of a wavelength less than a predefined wavelength and to block light of a wavelength larger than the predefined wavelength;
    a moving device configured to move the first filter between a first position on a light path of the first light from the first light source such that the apparatus is configured to output the first light filtered by the first filter as the output light and a second position such that the apparatus is configured to output the first light without having passed through any filter filtering out more than 30% of a light intensity of any wavelength in a wavelength range between 680 nm and 720 nm as the output light; wherein
    the predefined wavelength is in a range between 689 nm and 700 nm;
    an intensity of the first light at a wavelength larger than the predefined wavelength is at least 50% of an intensity of the first light at the peak wavelength.

7. An imaging system comprising
    the illumination apparatus according to claim 1, and
    an imaging device configured to image a scene on a first imaging surface if the scene is illuminated by the output light from the illumination apparatus.

8. The imaging system according to claim 7, wherein the imaging device comprises
    an excitation light cut filter configured to block light from the scene having a wavelength of less than a preset wavelength such that it does not reach the first imaging surface and to pass light from the scene having a wavelength larger than the preset wavelength such that it reaches the first imaging surface, and
    the preset wavelength is in a range between 690 nm and 700 nm.

9. The imaging system according to claim 7, further comprising
a first image sensor arranged at the first imaging surface.

10. The imaging system according to claim 9, further comprising
a further dichroic mirror configured to split the light from the scene such that the light from the scene having the wavelength larger than the preset wavelength reaches the imaging surface and such that other light having a wavelength shorter than a minimum wavelength reaches a second imaging surface different from the first imaging surface;
a second image sensor arranged at the second imaging surface; and wherein,
if the imaging device comprises the excitation light cut filter, the excitation light cut filter is configured to pass light having a wavelength of less than the minimum wavelength; and
the minimum wavelength is less than the preset wavelength by at least 20 nm.

11. An endoscope, comprising
the illumination apparatus according to claim 1, and
a rigid tip portion arranged at a distal end of the endoscope; wherein
the rigid tip portion of the endoscope is configured to output the output light from the illumination apparatus.

12. The endoscope according to claim 11, wherein the rigid tip portion comprises the illumination apparatus.

13. The endoscope according to claim 11, further comprising
an optical fiber configured to transmit the output light from the illumination apparatus to the rigid tip portion; wherein
the illumination apparatus is arranged at a proximal end of the endoscope or outside the endoscope.

* * * * *